United States Patent [19]
Bezwada et al.

[11] Patent Number: 5,133,739
[45] Date of Patent: Jul. 28, 1992

[54] SEGMENTED COPOLYMERS OF ε-CAPROLACTONE AND GLYCOLIDE

[75] Inventors: Rao S. Bezwada, Whitehouse Station; Dennis D. Jamiolkowski, Long Valley; Shalaby W. Shalaby, Lebanon, all of N.J.

[73] Assignee: Ethicon, Inc., Somerville, N.J.

[21] Appl. No.: 698,358

[22] Filed: May 13, 1991

Related U.S. Application Data

[63] Continuation-in-part of Ser. No. 475,619, Feb. 16, 1990, abandoned.

[51] Int. Cl.$^5$ .............................................. C08G 63/82
[52] U.S. Cl. .................................... 606/230; 606/231; 528/357
[58] Field of Search ............... 606/228, 229, 230, 231; 528/354, 357, 358

[56] References Cited

U.S. PATENT DOCUMENTS

| | | | |
|---|---|---|---|
| 3,736,646 | 6/1973 | Schmitt et al. | 606/226 |
| 4,137,921 | 2/1979 | Okuzumi et al. | 606/230 |
| 4,300,565 | 11/1981 | Rosensaft et al. | |
| 4,605,730 | 8/1986 | Shalaby et al. | |
| 4,643,734 | 2/1987 | Lin | 623/16 |
| 4,700,704 | 10/1987 | Jamiolkowski et al. | |
| 4,788,979 | 12/1988 | Jarrett et al. | 606/230 |

Primary Examiner—Stephen C. Pellegrino
Assistant Examiner—Michael Rafa
Attorney, Agent, or Firm—Matthew S. Goodwin

[57] ABSTRACT

Crystalline copolymer comprising the reaction product of: a) a predominant amount of a high molecular weight prepolymer of ε-caprolactone and glycolide, and b) the balance glycolide. A surgical device such as a surgical filament, in particular a surgical suture, prepared by injection molding or melt spinning the crystalline copolymer.

14 Claims, No Drawings

SEGMENTED COPOLYMERS OF ε-CAPROLACTONE AND GLYCOLIDE

This is a continuation-in-part, of application Ser. No. 475,619, filed Feb. 6, 1990. Abandoned May 13, 1991.

BACKGROUND OF THE INVENTION

This invention relates to crystalline copolymers of ε-caprolactone and glycolide. More specifically, it relates to crystalline copolymers of ε-caprolactone and glycolide prepared in a controlled two stage polymerization process which are suitable for the preparation of surgical articles, especially monofilament sutures.

The preparation of surgical articles from synthetic, bioabsorbable polymers by molding or spinning fibers is well known. The most widely used polymers for the preparation of such articles are derived from hydroxy acids and their condensation products, anhydrous cyclic esters commonly referred to as lactones. Among the most widely studied lactones for preparing bioabsorbable polymers for surgical articles are ε-caprolactone, lactide and glycolide. Naturally, recent attention has been focused on improving the physical and biological properties of polymers and copolymers derived from these specific lactones.

The most recent attempt to optimize the properties of copolymers of ε-caprolactone and glycolide is disclosed in U.S. Pat. Nos. 4,605,730 and 4,700,704. These patents describe single and two stage polymerization processes for preparing the copolymers. Of particular interest is the two stage polymerization process. Specifically, the patents disclose in a number of different examples first preparing a low molecular weight prepolymer of ε-caprolactone and glycolide, and then polymerizing in situ the resulting prepolymer with glycolide to produce a crystalline copolymer.

Unfortunately, the crystalline copolymers prepared in the two stage process described in these patents do not provide the most desirable physical and biological properties when fabricated into surgical articles. Most significantly, when the copolymers are spun to prepare fibers exhibiting an acceptable biological profile for surgical sutures, the fibers are quite stiff. This stiffness, or lack of compliance, makes it difficult to tie knots from sutures prepared from these fibers, and additionally, reduces the knot integrity when knots are tied because of the tendency for the knot to become loose. Furthermore, the physical properties of fibers prepared from these crystalline copolymers, e.g. straight and knot tensile strength, or their biological properties, e.g. in vivo breaking strength retention (BSR), may not be adequate to meet the requirements for a suitable surgical suture in some surgical procedures.

In view of the generally less desirable compliance characteristics of crystalline copolymers of ε-caprolactone and glycolide, useful surgical articles, and in particular monofilament surgical sutures, from such copolymers have not been developed. Typically, the lack of compliance of fibers spun from such copolymers would require the braiding or twisting of individual fibers to prepare a multifilament suture. Multifilament sutures are disadvantageous because, among other things, they often require a surface coating for enhancing the lubricity and smoothness of the suture surface to prevent trauma to tissue during suturing.

Therefore, in view of the deficiencies of the prior art, it would be most desirable to prepare a copolymer of ε-caprolactone and glycolide which can be fabricated into useful surgical articles. In particular, it would be desirable to prepare such a copolymer which can be spun into fibers, and exhibit outstanding compliance as well as excellent physical and biological properties for the preparation of monofilament sutures.

SUMMARY OF THE INVENTION

In one aspect, the invention is a crystalline copolymer comprising the reaction product of: a) a predominant amount of a prepolymer of ε-caprolactone and glycolide, and b) the balance glycolide. The prepolymer of ε-caprolactone and glycolide from which the crystalline copolymer is prepared has an inherent viscosity between about 0.6 to about 2.0 deciliters per gram (dl/g) as measured in a 0.1 g/dl solution of hexafluoroisopropanol (HFIP) at 25° C.

In another aspect, the invention is a surgical filament prepared by melt spinning the crystalline copolymer described above.

In yet another aspect, the invention is a surgical device fabricated from the crystalline copolymer described above.

Surprisingly, the controlled two stage preparation of the crystalline copolymer from a relatively high molecular weight prepolymer of ε-caprolactone and glycolide (as reflected in the inherent viscosity of the prepolymer) yields a copolymer which can be readily molded into surgical devices or melt spun into fibers having an outstanding combination of physical and biological properties. Fibers prepared from these crystalline copolymers exhibit significantly improved compliance, as measured by Young's Modulus, relative to the compliance exhibited by fibers prepared from the crystalline copolymers of ε-caprolactone and glycolide in the two stage polymerization process described in the prior art.

Additionally, these fibers exhibit excellent straight and knot tensile strength in relation to fibers prepared from other bioabsorbable polymers and copolymers typically used for surgical articles, and also exhibit acceptable in vivo BSR for numerous surgical applications.

The crystalline copolymers of this invention are useful for the preparation of absorbable surgical filaments, especially absorbable monofilament surgical sutures, although these copolymers may find use in the preparation of other surgical devices. For example, the copolymers may be used for the preparation of surgical meshes, components for surgical staples, hemostatic clips, and the like.

DETAILED DESCRIPTION OF THE INVENTION

In a preferred embodiment, the crystalline copolymers of this invention have a molecular weight as reflected in their inherent viscosity and the ability to develop a degree of crystallinity which render the copolymers suitable for extrusion into fibers or films and for injection molding into surgical devices such as staples. Advantageously, the crystallinity of the copolymers is greater than about 15 percent as measured by x-ray diffraction, so that surgical devices prepared from the copolymer can maintain their dimensional integrity at the elevated temperatures one might encounter during storage. Preferably, the inherent viscosity of the crystalline copolymers ranges from about 0.8 to about 2.5, more preferably from about 1.4 to about 1.8 dl/g in a 0.1 g/dl solution of HFIP at 25° C. A copolymer with an inherent viscosity below about 0.8 dl/g generally lacks sufficient viscosity to provide suitable melt strength for extrusion or molding, and a copolymer with an inherent viscosity above about 2.5 dl/g is generally too viscous for melt processing at the temperatures desired to avoid polymer degradation.

The crystalline copolymers are referred to in the Examples following this detailed description as segmented copolymers. While not wishing to be bound by any particular theory, we envision the polymer chains of the copolymer of this invention to be made up of "soft" blocks of a copolymer of $\epsilon$-caprolactone and glycolide, which are segmented with relatively shorter "hard" blocks of glycolide homopolymer. Generally, the $\epsilon$-caprolactone/glycolide copolymer soft blocks provide the copolymer of this invention with its unexpectedly improved compliance, and the glycolide homopolymer hard blocks enhance the physical properties and in vivo BSR of the copolymer.

A predominant amount of prepolymer generally refers to an amount of prepolymer greater than or equal to 50 mole percent of the composition from which the crystalline copolymer of this invention is derived. An amount less than 50 mole percent prepolymer will typically yield a copolymer which is too stiff. Preferably, the amount of prepolymer is between about 55 to about 95, more preferably from about 60 to about 80 mole percent. Although an amount of prepolymer greater than 95 mole percent can be used in the practice of this invention, it is less desirable because such high amounts of prepolymer may adversely affect the physical properties and in vivo BSR of the copolymer.

The inherent viscosity of the prepolymer is a significant factor in the improvement observed for the compliance of the copolymers relative to the prior art, and should range between about 0.6 and about 2.0 dl/g in HFIP. If the inherent viscosity were below about 0.6 dl/g, then the molecular weight of the prepolymer at a predetermined desirable copolymer composition would be too low and the resulting copolymer would lack an appropriate molecular weight. At a copolymer molecular weight necessary for extrusion and molding, a prepolymer with an inherent viscosity below about 0.6 dl/g would require an excess amount of glycolide during the second stage of polymerization, ultimately resulting in a copolymer with inadequate compliance. If the inherent viscosity were above about 2.0 dl/g, then the prepolymer would be too viscous to readily form a homogeneous solution with the glycolide component of the copolymer composition, and an undesirable two phase copolymer would likely result. Preferably, the inherent viscosity of the prepolymer is between about 0.8 to about 1.6 dl/g.

The mole ratio of $\epsilon$-caprolactone to glycolide in the prepolymer is preferably between about 45:55 to about 30:70, more preferably between about 60:40 to about 40:60. Generally, if the mole ratio were below about 30:70, then the crystalline copolymer prepared from such a prepolymer would be less compliant than desired. If the mole ratio of $\epsilon$-caprolactone to glycolide in the prepolymer were greater than 45:55, then the solubility of the prepolymer in the glycolide monomer and its compatibility with the developing hard polyglycolide blocks would not be adequate to prepare a single phase copolymer with the most desirable properties.

As a general rule, when the mole ratio of $\epsilon$-caprolactone to glycolide in the prepolymer is between about 45:55 to about 30:70, the prepolymer will exhibit a degree of crystallinity between about 2 to 15 percent as measured by x-ray diffraction and a melting temperature less than 120° C. Such a prepolymer can readily form a homogeneous solution with glycolide at an acceptable temperature and polymerize with glycolide to form the desired crystalline copolymer. However, it must be understood that a prepolymer with a mole ratio outside this range can be used to prepare the crystalline copolymers of this invention, although to do so would be less predictable and desirable.

The crystalline copolymers of this invention can be prepared by first preparing the prepolymer of $\epsilon$-caprolactone and glycolide, and then polymerizing the prepolymer with glycolide. The prepolymer can be prepared by polymerizing the desired proportions of $\epsilon$-caprolactone and glycolide in the presence of an organometallic catalyst and an initiator at elevated temperatures. The organometallic catalyst is preferably a tin-based catalyst, e.g. stannous octoate, and is present in the monomer mixture at a mole ratio of monomer to catalyst ranging from about 15,000 to 80,000/1. The initiator is typically an alkanol, a glycol, a hydroxyacid, or an amine, and is present in the monomer mixture at a mole ratio of monomer to initiator ranging from about 250 to 2000/1. The polymerization is typically carried out at a temperature range from 120° C. to 200° C., preferably 160° C.-190° C., until the desired molecular weight and viscosity are achieved.

In the preferred embodiment, the conversion of monomer to prepolymer is greater than 95 mole percent to avoid the formation of undesirable copolymeric hard segments of $\epsilon$-caprolactone and glycolide during the subsequent polymerization with glycolide. Preferably, the conversion of monomer to prepolymer is greater than 98 mole percent. Conversion of monomer to prepolymer is measured by weight loss methods, e.g. at 110° C. in vacuo until constant weight is achieved.

After the prepolymer is prepared, the temperature of the reaction mixture is increased to about 230° C., and then molten glycolide is added with vigorous stirring to form a homogeneous solution of the glycolide in the prepolymer. The polymerization reaction is allowed to proceed for about 15 to 30 minutes at an elevated temperature, and then the temperature is lowered to about 200° C. to avoid possibly degrading polycaprolactone moieties. The polymerization may continue at this temperature until the desired molecular weight and percent conversion is achieved for the copolymer, which will typically take about 2 to 3 hours.

Once the desired crystalline copolymer is prepared, absorbable filaments exhibiting the requisite properties for use as monofilament surgical sutures may be prepared using conventionally accepted methods well known in the art by first melt extruding the copolymer through a spinnerette to prepare fibers, drawing the fibers to create orientation, and then annealing the oriented fibers to enhance dimensional stability. Optimun annealing time and temperature for maximum in vivo BSR and dimensional stability is readily determined by simple experimentation for each fiber composition. Additionally, the sutures prepared from such monfilament fibers can be attached, if desired, to one or more needles.

In preferred embodiments of this invention, absorbable surgical monofilaments prepared from the crystalline copolymers of this invention have a straight tensile strength of at least 50,000 psi, preferably at least 70,000 psi, and a knot tensile strength of at least 30,000 psi, preferably at least 40,000 psi. The Young's Modulus for preferred embodiments is typically below 500,000 psi, preferably below 300,000 psi, and more preferably below 150,000.

In the Examples which follow, the in vivo BSR and fiber properties shown in the tables, e.g. straight and knot tensile strength, percent elongation and Young's Modulus, are determined using the conventional methods described in U.S. Pat. Nos. 4,653,497 and 4,838,267. In vitro BSR is determined by measuring the percent of original straight tensile strength remaining after the indicated number of days in a phosphate buffer with a pH of 7.27 at 50° C. PCL and PGA refer to polymerized moieties of ε-caprolactone and glycolide, respectively. These Examples are illustrative only and are not intended to limit the scope of the claimed invention, since additional embodiments within the scope of the claimed invention will become readily apparent to those skilled in the art.

The data shown in the tables from the Examples illustrates overall the outstanding compliance characteristics, as measured by the Young's Modulus, of monofilaments prepared from the crystalline copolymers of this invention. The outstanding compliance of the monofilaments is achieved without sacrificing their physical properties or BSR, and in fact, the values shown for these properties are excellent standing alone.

EXAMPLE 1

SEGMENTED COPOLYMER OF 30/70 PCL/PGA BY MOLE OVERALL FROM A 50/50 PCL/PGA BY MOLE PREPOLYMER

A flame dried 250 ml three neck flask is charged with 34.24 gm (0.300 mole) ε-caprolactone, 34.82 gm (0.300 mole) glycolide, 0.114 ml (1.2 mmole/mole of total monomer) distilled diethylene glycol and 0.0505 ml stannous octoate (0.33 molar solution in toluene). The flask is fitted with a flame dried mechanical stirrer and an adapter. The reactor is purged three times before being vented with nitrogen. The reaction mixture is heated to 190° C. under nitrogen, and maintained at this temperature for about 16 to 18 hours. The percent conversion of monomer to prepolymer is 99.5 mole percent. The inherent viscosity (I.V.) of the resulting prepolymer is 1.52 dl/g and the melting point is 49° C.

46.43 Grams (0.4 mole) of molten glycolide is added to the prepolymer in the reaction flask. The temperature of the reaction mixture is raised to 230° C. to dissolve the prepolymer into the molten glycolide. After about 10 to 15 minutes, the temperature of the reaction mixture is dropped to 200° C. Total reaction time at 200° C.-230° C. is about 2 hours. The copolymer is isolated, ground, and dried 16 hours/110° C./0.1 mm Hg. to remove any unreacted monomers. A weight loss of 0.6% is observed.

The copolymer has a melting range of about 180° C.-219° C. by hot stage microscopy, and an inherent viscosity of 2.15 dl/g in (HFIP) and a PCL/PGA molar ratio of 30.2/69.8 by NMR.

EXAMPLE 2

SEGMENTED COPOLYMER OF 30/70 PCL/PGA BY MOLE OVERALL FROM A 40/60 PCL/PGA BY MOLE PREPOLYMER

The procedure described in Example 1 is substantially reproduced, and a prepolymer with an I.V. of 1.48 is prepared by reacting 34.24 g (0.300 mole) ε-caprolactone with 52.23 g (0.450 mole) glycolide. The percent conversion of monomer to prepolymer is 98.1 mole percent, and the prepolymer melting point is 106° C. The prepolymer is polymerized with 29.02 g (0.250 mole) glycolide to prepare the copolymer. A weight loss of 1.0% is observed.

The copolymer has a melting range of 182° C.-209° C. by hot stage microscopy, an inherent visocity of 1.68 dl/g in HFIP and a PCL/PGA molar ratio of 27.4/71.0 by NMR.

EXAMPLES 3 & 4

The copolymers described in Examples 1 and 2 are extruded into monofilament fibers shown as Examples 3 and 4, respectively, using a capillary rheometer according generally to the procedures described in U.S. Pat. No. 4,838,267, except that the extruded filaments may require up to two weeks storage time at room temperature before orientation to allow the desired crystallization to occur. The physical properties of oriented and annealed fibers are shown in Table I. The orientation conditions are as follows:

|  | Stage 1 | Stage 2 | Total Draw Ratio |
|---|---|---|---|
| Example 3 | 5.0 × (50° C.) | 1.325 × (78° C.) | 6.6 |
| Example 4 | 5.0 × (41° C.) | 1.40 × (79° C.) | 7.0 |

The annealing conditions for the oriented fibers are 6 hours at 110° C., restrained from shrinkage.

TABLE I

|  | Example 3 | | Example 4 | |
|---|---|---|---|---|
|  | oriented | annealed | oriented | annealed |
| Fiber Properties |  |  |  |  |
| Diameter, mils | 7.8 | 8.0 | 7.3 | 7.3 |
| Str. Tensile, kpsi | 85 | 79 | 97 | 89 |
| Knot strength, kpsi | 35 | 43 | 58 | 55 |
| Percent Elongation | 72 | 44 | 67 | 40 |
| Young's Modulus, kpsi | 24 | 150 | 28 | 52 |
| In Vitro BSR, percent at: |  |  |  |  |
| 4 days | — | 36 | — | 30 |
| 7 days | — | 8 | — | 9 |

EXAMPLES 5–8

The procedure described in Example 1 is substantially reproduced to prepare several segmented copolymers of 30/70 PCL/PGA by mole overall from a 40/60 PCL/PGA by mole prepolymer. The properties of these copolymers are summarized in Table II.

TABLE II

| PROPERTIES OF CAPROLACTONE/GLYCOLIDE COPOLYMERS: 40/60 PREPOLYMER AND 30/70 OVERALL | | | | |
|---|---|---|---|---|
| EXAMPLE | 5 | 6 | 7 | 8 |
| Prepolymer I.V., dl/g | 1.55 | 1.51 | 1.54 | 1.57 |
| Prepolymer Melting point[1], °C. | 109 | 105 | 110 | 92 |
| comp. by NMR % mole | 29.6/70.0/0.4 | 29.8/69.8/0.5 | 29.4/69.6/0.9 | 29.6/69.7/0.7 |

TABLE II-continued

PROPERTIES OF CAPROLACTONE/GLYCOLIDE COPOLYMERS:
40/60 PREPOLYMER AND 30/70 OVERALL

| EXAMPLE | 5 | 6 | 7 | 8 |
|---|---|---|---|---|
| PCL/PGA/monomer | | | | |
| Copolymer I.V., dl/g | 1.71 | 1.78 | 1.78 | 1.87 |
| Copolymer Melting Point[1], °C. | 174 | 183 | 181 | 186 |
| FIBER PROPERTIES (after annealing) | | | | |
| Ann. 6 hrs/110° C./0% shrinkage | | | | |
| Diameter, mils | 7.3 | 7.2 | 7.0 | 7.1 |
| Str. Strength, psi | 94,293 | 90,395 | 104,515 | 95,446 |
| Knot Strength, psi | 60,872 | 54,443 | 48,358 | 43,795 |
| % Elong. | 54 | 50 | 46 | 41 |
| Y. M., psi | 38,626 | 78,511 | 65,750 | 50,111 |
| IN VITRO BSR, percent at: | | | | |
| 4 days | 24 | 39 | 33 | 34 |
| 7 days | 3 | 4 | 7 | 8 |
| IN VIVO BSR, percent at: | | | | |
| 14 days | — | 28 | 37 | — |
| 21 days | — | 10 | 13 | — |
| 28 days | — | 2 | 2 | — |

[1]Determined by hot stage microscopy.

EXAMPLES 9-12

The procedure described in Example 1 is substantially repeated to prepare four segmented copolymers of 30/70 PCL/PGA by mole overall from a 45/55 PCL/PGA by mole prepolymer. The properties of these copolymers are summarized in Table III.

TABLE III

PROPERTIES OF CAPROLACTONE/GLYCOLIDE COPOLYMERS:
45/55 PREPOLYMER AND 30/70 OVERALL

| EXAMPLE | 9 | 10 | 11 | 12 |
|---|---|---|---|---|
| Prepolymer I.V., dl/g | 1.45 | 1.38 | 1.47 | 1.60 |
| comp. by NMR % mole | 27.8/72.2/0 | 29.0/70.8/0.2 | 28.5/70.8/0.7 | 28.8/70.9/0.3 |
| PCL/PGA/monomer | | | | |
| Copolymer I.V., dl/g | 1.63 | 1.40 | 1.67 | 1.73 |
| Copolymer Melting Point[1], °C. | 176–181 | 184 | 186 | 185–189 |
| FIBER PROPERTIES (after annealing) | | | | |
| Ann. 6 hrs/110° C./0% shrinkage | | | | |
| Diameter, mils | 7.7 | 7.1 | 7.6 | 7.4 |
| Str. Strength, psi | 94,700 | 93,956 | 100,296 | 101,142 |
| Knot Strength, psi | 50,893 | 36,875 | 43,866 | 55,802 |
| % Elong. | 56 | 45 | 51 | 54 |
| Y. M., psi | 34,487 | 52,231 | 43,645 | 42,456 |
| IN-VITRO BSR, percent at: | | | | |
| 4 days | 31 | 24 | 30 | 43 |
| 7 days | 8 | 4 | 6 | 10 |
| IN-VIVO BSR, percent at: | | | | |
| 14 days | — | — | — | 30 |
| 21 days | — | — | — | 10 |
| 28 days | — | — | — | — |

[1]Determined by hot stage microscopy.

EXAMPLE 13

SEGMENTED COPOLYMER OF 24/76 PCL/PGA BY MOLE OVERALL FROM A 40/60 PCL/PGA BY MOLE PREPOLYMER

The procedure described in Example 1 is substantially reproduced, and a prepolymer with an I.V. of 1.42 is prepared by reacting 34.24 gm (0.300 mole) ε-caprolactone with 52.23 gm (0.450 mole) glycolide. The conversion of monomer to prepolymer is 98.6 mole percent. The prepolymer is polymerized with 58.04 gm (0.500 mole) glycolide to prepare the copolymer. A weight loss of 1.0% is observed.

The copolymer has a melting range of 193° C.-202° C. by hot stage microscopy, and inherent viscosity of 1.75 dl/g in HFIP and PCL/PGA mole ratio of 25.7/74.3 by NMR.

EXAMPLE 14

The copolymer described in Example 13 is extruded into monofilament fibers using a capillary rheometer according generally to the procedure described in U.S. Pat. No. 4,838,267, except that the extrudate filaments may require up to two weeks storage time at room temperature before orientation to allow the desired crystallization to occur. The physical properties of oriented and annealed fibers are shown in Table V. The orientation conditions are as follows:

| | Stage 1 | Stage 2 | Total Draw Ratio |
|---|---|---|---|
| Example 14 | 5× at 54° C. | 1.35× at 83° C. | 6.75× |

The annealing conditions for the oriented fibers are 6 hours at 110° C., restrained from shrinkage.

TABLE IV
PROPERTIES OF CAPROLACTONE/ GLYCOLIDE COPOLYMER: 40/60 PREPOLYMER AND 24/76 OVERALL

| | Example 14 | |
|---|---|---|
| Fiber Properties | oriented | annealed |
| Diameter, mils | 7.7 | 7.6 |
| Str. Tensile, kpsi | 101 | 112 |
| Knot strength, kpsi | 61 | 56 |
| Percent Elongation | 58 | 47 |
| Young's Modulus, kpsi | 60 | 156 |
| In-Vitro BSR, percent at: | | |
| 4 days | — | 53 |
| 7 days | — | 10 |

EXAMPLE 15

SEGMENTED COPOLYMER OF 20/80 PCL/PGA BY MOLE OVERALL FROM A 40/60 PCL/PGA BY MOLE PREPOLYMER

The procedure described in Example 1 is substantially reproduced, and a prepolymer with an I.V. of 1.41 is prepared by reacting 45.66 gm (0.4 mole) ε-caprolactone with 69.64 g (0.600 mole) glycolide. The conversion of monomer to prepolymer is 99.3 mole percent. The prepolymer is polymerized with 116.07 gm (1.0 mole) glycolide to prepare this copolymer. A weight loss of 0.8% is observed.

The copolymer has melting range of 188° C.–203° C., by hot stage microscopy, an inherent viscosity of 1.70 dl/g in HFIP, and PCL/PGA mole ratio of 22.2/77.8 by NMR.

EXAMPLE 16

The copolymer described in Example 15 is extruded into monofilament fibers. The physical properties of oriented and annealed fibers are shown in Table V. The orientation conditions are as follows:

| | Stage 1 | Stage 2 | Total Draw Ratio |
|---|---|---|---|
| Example 16 | 5× at 47° C. | 1.25× at 74° C. | 6.25× |

The annealing conditions for the oriented fibers are 6 hours/110° C./0% relaxation.

TABLE V
PROPERTIES OF CAPROLACTONE/ GLYCOLIDE COPOLYMER: 40/60 PREPOLYMER AND 20/80 OVERALL

| | Example 16 | |
|---|---|---|
| Fiber Properties | oriented | annealed |
| Diameter, mils | 7.7 | 7.6 |
| Str. Tensile, kpsi | 107 | 106 |
| Knot strength, kpsi | 67 | 38 |
| Percent Elongation | 35 | 26 |
| Young's Modulus, kpsi | 105 | 487 |

What is claimed is:

1. A crystalline copolymer comprising the reaction product of:
   (a) a predominant amount of a prepolymer of ε-caprolactone and glycolide wherein the inherent viscosity of the prepolymer is between about 0.6 to about 2.0 dl/g as measured in a 0.1 g/dl solution of HFIP at 25° C. and the mole ratio of ε-caprolactone to glycolide in the prepolymer is between 45:55 to about 30:70, and
   (b) the balance glycolide.

2. The crystalline copolymer of claim 1 wherein the amount of the prepolymer is between about 55 to about 95 mole percent.

3. The crystalline copolymer of claim 2 wherein the inherent viscosity of the prepolymer is between about 0.8 to about 1.6 dl/g.

4. The crystalline copolymer of claim 3 wherein the prepolymer conversion of monomer to prepolymer is greater than 95 mole percent.

5. The crystalline copolymer of claim 4 wherein the prepolymer conversion of monomer to prepolymer is greater than 98 mole percent.

6. The crystalline copolymer of claim 5 wherein the amount of the prepolymer is between about 60 to about 80 mole percent.

7. A surgical filament prepared by melt spinning a crystalline copolymer of:
   (a) a predominant amount of a prepolymer of ε-caprolactone and glycolide wherein the inherent viscosity of the prepolymer is between about 0.6 to about 2.0 dl/g as measured in a 0.1 g/dl solution of HFIP at 25° C. and the mole ratio of ε-caprolactone to glycolide in the prepolymer is between 45:55 to about 30:70, and
   (b) the balance glycolide.

8. The surgical filament of claim 7 wherein the Young's Modulus is less than 300,000 psi.

9. The surgical filament of claim 8 wherein the Young's Modulus is less than 150,000 psi.

10. The surgical filament of claim 9 wherein the straight tensile strength is at least 50,000 psi.

11. The surgical filament of claim 10 wherein the knot tensile strength is at least 30,000 psi.

12. The surgical filament of claim 11 in the form of a monofilament.

13. The surgical filament of claim 12 in the form of a suture.

14. The surgical filament of claim 13 wherein the suture is attached to at least one needle.

* * * * *